(12) United States Patent
Webb et al.

(10) Patent No.: US 9,284,400 B2
(45) Date of Patent: Mar. 15, 2016

(54) ASPARTIC RESINS

(71) Applicants: Arthur A Webb, Bethesda, MD (US); Jozef Verborgt, Dunedin, FL (US); Keith E Lucas, Upper Marlboro, MD (US)

(72) Inventors: Arthur A Webb, Bethesda, MD (US); Jozef Verborgt, Dunedin, FL (US); Keith E Lucas, Upper Marlboro, MD (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 13/832,126

(22) Filed: Mar. 15, 2013

(65) Prior Publication Data

US 2014/0275407 A1    Sep. 18, 2014

(51) Int. Cl.

| | | |
|---|---|---|
| *B05D 1/34* | (2006.01) | |
| *B05D 3/02* | (2006.01) | |
| *B05D 3/10* | (2006.01) | |
| *B05D 7/24* | (2006.01) | |
| *C07C 229/22* | (2006.01) | |
| *C07C 229/24* | (2006.01) | |
| *C07C 229/26* | (2006.01) | |
| *C08L 75/02* | (2006.01) | |
| *C08G 18/38* | (2006.01) | |
| *C08G 18/76* | (2006.01) | |
| *C09D 175/02* | (2006.01) | |

(52) U.S. Cl.
CPC .............. *C08G 18/3821* (2013.01); *B05D 1/34* (2013.01); *B05D 3/02* (2013.01); *B05D 3/108* (2013.01); *B05D 7/24* (2013.01); *C07C 229/22* (2013.01); *C07C 229/24* (2013.01); *C07C 229/26* (2013.01); *C08G 18/765* (2013.01); *C08L 75/02* (2013.01); *C09D 175/02* (2013.01); *B05D 2401/31* (2013.01); *B05D 2503/00* (2013.01)

(58) Field of Classification Search
CPC ............ B05D 1/34; B05D 3/02; B05D 3/108; B05D 7/24; B05D 2401/31; B05D 2503/00; C07C 229/22; C07C 229/24; C07C 229/26; C08L 75/02; C09D 175/02; C08G 18/3821; C08G 18/765
USPC ........... 524/589, 590; 528/44, 61, 76, 84, 64, 528/68; 427/372.2, 385.5, 421.1; 560/129, 560/170, 171
See application file for complete search history.

(56) References Cited

U.S. PATENT DOCUMENTS

| | | | |
|---|---|---|---|
| 2,778,833 | A | 1/1957 | Surrey |
| 3,158,635 | A | 11/1964 | Kerzerian et al. |
| 3,959,289 | A | 5/1976 | Hall et al. |
| 5,126,170 | A | 6/1992 | Zwiener et al. |
| 5,243,012 | A | 9/1993 | Wicks et al. |
| 5,412,056 | A | 5/1995 | Zwiener et al. |
| 5,516,873 | A | 5/1996 | Hicks et al. |
| 5,580,945 | A | 12/1996 | Wade et al. |
| 6,005,062 | A | 12/1999 | Hansen et al. |
| 6,605,684 | B2 * | 8/2003 | Primeaux et al. ............... 528/68 |
| 6,613,389 | B2 | 9/2003 | Li et al. |
| 7,001,948 | B2 | 2/2006 | Gupta et al. |
| 7,196,154 | B2 | 3/2007 | Bonilla |
| 2011/0136587 | A1 | 6/2011 | Ricci et al. |

FOREIGN PATENT DOCUMENTS

CN          102250343       * 11/2011

OTHER PUBLICATIONS

Machine English translation of CN 102250343, Xinli et al., Nov. 2011.*
CAS Registry Entry (2011).

(Continued)

*Primary Examiner* — Patrick Niland
(74) *Attorney, Agent, or Firm* — US Naval Research Laboratory; Joseph T. Grunkemeyer

(57) ABSTRACT

A composition having a polyurea made by reacting a polyisocyanate with one of the below compounds. The value x is 2 or 3. A method of: providing a polyisocyanate and one of the below compounds, spraying the polyisocyanate and the compound with a plural component pump onto a surface to form a mixture, and allowing the mixture to cure to a polyurea.

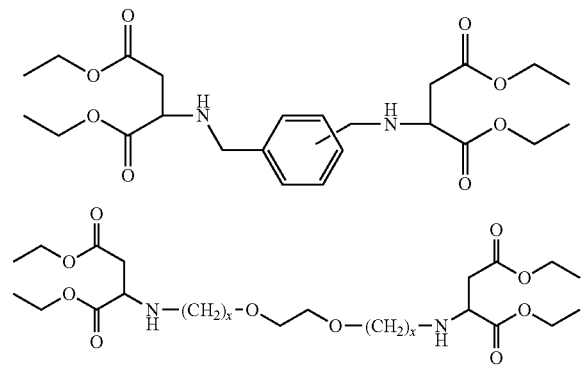

5 Claims, No Drawings

(56) References Cited

OTHER PUBLICATIONS

Khetan et al. "Reactions of dimethyl acetylenedicarboxylate. III. Reactions with diamines and anthranilic acid" Canadian Journal of Chemistry, 1969, 47(19): 3545-3551.

L'italien et al., "2-Hydroxy-3-alkylquinoxalines" J. Am. Chem. Soc. 1951, 73, 3246-7.

López-Ruiz et al., "Synthesis of Nitrogen-, Oxygen- and Sulphur-containing Tripodal Ligands with a Trimethylbenzene Core" J. Mex. Chem. Soc. 2011, 55(3), 168-175.

Piotrowska et al., "Synthesis and chelating properties of carboxylic derivatives of aromatic amines" Roczniki Chemii 46(7/8) 1323-33 (1972) (Search result listing only).

Ruggli et al., "Über Derivate des m- und p-Phenylen-diamins sowie des 6-Amino-oxindols" Helvetica Chimica Acta 20, 373-386 (1937) (German with English translation of Abstract).

Rutkauskas et al., "Cyclization of the Reaction Products of p-Phenylenediamine with Maleic Acid" Chemistry of Heterocyclic Compounds, vol. 40, No. 6, 2004.

Simig et al., "Simple and condensed ?-lactams. II. The synthesis of new diethyl 4-oxoazetidine-2,2-dicarboxylates and some manipulations of their functional groups and N-substituents" Acta Chimica Hungarica 119(1) 17-32 (1985) (Search result listing only).

Surrey et al., "The Synthesis of Some 4,10-Disubstituted-1,7-phenanthroline Derivatives" J. Am. Chem. Soc., 1954, 76 (4), 1109-1113.

* cited by examiner

ASPARTIC RESINS

TECHNICAL FIELD

The present disclosure is generally related to aspartic resin-based coatings.

DESCRIPTION OF RELATED ART

Polyaspartic ester resins have been reacted with polyisocyanates to form polyureas. However, the polyaspartics generally have sterically hindered amine groups which produce long cure times.

There are currently no solvent free top coats with good weatherability on the market for the marine industry. Existing technology is based on silicone alkyds with high solvent content. Such silicone alkyds are brush or roller applied at dft's of 2-3 mills. They do require a primer and are over coated many times during the life time of a ship.

BRIEF SUMMARY

Disclosed herein is composition comprising a polyurea made by reacting a polyisocyanate with a compound selected from Eqs. (1) and (2).

Also disclosed herein is a method comprising: providing a polyisocyanate and a compound selected from Eqs. (1) and (2); spraying the polyisocyanate and the compound with a plural component pump onto a surface to form a mixture; and allowing the mixture to cure to a polyurea.

Also disclosed herein is a compound having the formula of Eq. (2). The value x is 2 or 3.

DETAILED DESCRIPTION OF EXAMPLE EMBODIMENTS

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

Disclosed herein are fast curing, single coat coatings that may be total solvent-free and are based on aspartic resins.

These aspartic resins can be formulated in self extinguishing coatings for the interior of ships, weatherable top coats, or direct to metal coatings for the marine and or heavy duty industries. These coatings cure in minutes and can be spray applied using application technology not unlike the twin feed systems developed previously for the ballast tank coatings. They do form very hard, yet flexible films with good UV resistance.

The aspartic coatings have properties comparable to powder coatings but without the need for heat cure. They are insensitive to humidity during production and application, in contrast to the more classic polyurethane coatings.

Aspartics can be formulated into clear coatings for the automotive industry, heavy duty direct to metal, self extinguishing coatings, or top coats with a polyurethane like quality. Applications may include rail cars, heavy duty equipment, the OEM industry, marine and heavy duty anticorrosion markets like petrochemical, bridges, and power generation.

The aspartic resins may be made by a Michael addition of the appropriate diamine to diethyl maleate or diethyl fumarate as shown in Eqs. (3) and (4) for the maleate. Xylylene diamines and JEFFAMINE® EDR-148 and EDR-176 are commercially available amines. These amines may be the only isocyanate reactive compounds used to make the polyurea with no other amines present. The reaction is performed by a Michael addition reaction using methods and parameters known in the art of Michael reactions.

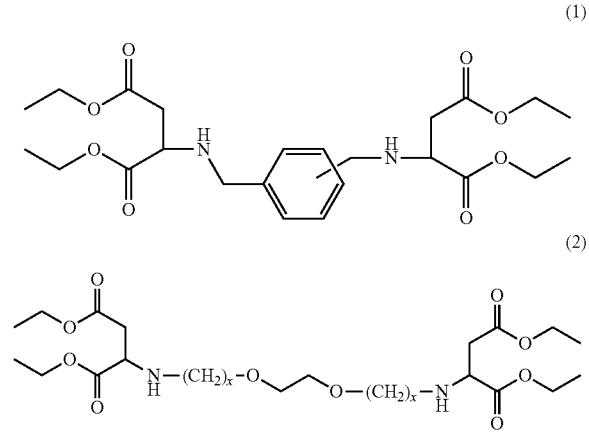

Once the resin is formed it is reacted with a polyisocyanate to form a polyurea. The isocyanate groups react with the amine groups in the standard way for forming substituted ureas as shown in Eq. (5). In this example the polyisocyanate is α,α,α',α'-tetramethylxylylene diisocyanate. The reaction may proceed at a rapid rate allowing for curing in less than 20-40 minutes. The reaction may be performed in the absence of solvent with a plural component pump.

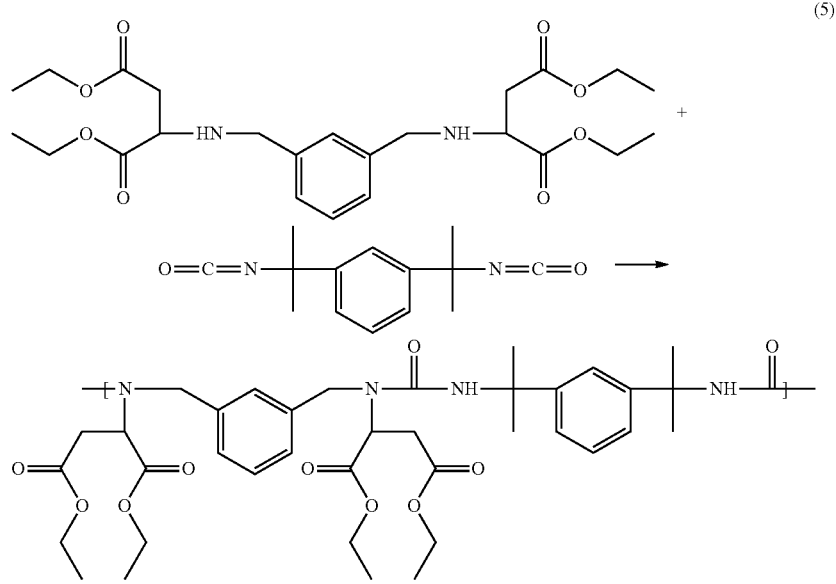

(5)

The polyisocyanate may have an equivalent weight of 100 to 200. Suitable polyisocyanates include, but are not limited to, α,α,α',α'-tetramethylxylylene diisocyanate and isophorone diisocyanate. The polyisocyanate may be an aliphatic isocyanate in that the isocyanate groups are directly bound to aliphatic moieties, though aromatic groups may also be present in the polyisocyanate.

The following examples are given to illustrate specific applications. These specific examples are not intended to limit the scope of the disclosure in this application.

EXAMPLE 1

MXDA aspartic resin—A glass reactor equipped with a mechanical stirrer was placed in a water bath and loaded with two mole equivalents of di-ethyl maleate (344 grams). A one mole equivalent of MXDA (136 grams) was added drop wise under mild cooling over a period of two hours. The reaction temperature should not exceed 40° C. The Michael addition reaction was almost complete after 10 hrs. It is however advantageous to store the product at ambient temperature for several days in order to get a complete reaction which is almost odor free. It can be advantageous to add a small excess of 3% of the amine in order to get a product totally free of the di-ethyl maleate smell. The MXDA aspartic resin was totally solvent free and can be formulated into solvent free top coats that will cure within minutes.

EXAMPLE 2

Jeffamine 148 aspartic resin—A glass reactor equipped with a mechanical stirrer was placed in a water bath and loaded with two mole equivalents of di-ethyl maleate (344 grams). A one mole equivalent of Jeffamine 148 (148 grams) was added drop wise under mild cooling over a period of two hours. The reaction temperature should not exceed 40° C. The Michael addition reaction was almost complete after 10 hrs. It is however advantageous to store the product at ambient temperature for several days in order to get a complete reaction which is almost odor free. It can be advantageous to add a small excess of 3% of the amine in order to get a product totally free of the di-ethyl maleate smell. The Jeffamine aspartic resin was totally solvent free and can be formulated into coatings that can be spray applied to the hulls of ships, cars, or rail underbodies. The Jeffamine 148 aspartic resin can be cured with various aliphatic isocyanates giving products with varying glass transitions. The glass transition can further be fine tuned by adding either plasticizers or co-resins.

EXAMPLE 3

Jeffamine 176 aspartic resin—A glass reactor equipped with a mechanical stirrer was placed in a water bath and loaded with two mole equivalents of di-ethyl maleate (344 grams). A one mole equivalent of Jeffamine 176 (176 grams) was added drop wise under mild cooling over a period of two hours. The reaction temperature should not exceed 40° C. The Michael addition reaction was almost complete after 10 hrs. It is however advantageous to store the product at ambient temperature for several days in order to get a complete reaction which is almost odor free. It can be advantageous to add a small excess of 3% of the amine in order to get a product totally free of the di-ethyl maleate smell. The Jeffamine aspartic resin was totally solvent free and can be formulated into coatings that can be spray applied to the hulls of ships, cars, or rail underbodies. The Jeffamine 148 aspartic resin can be cured with various aliphatic isocyanates giving products with varying glass transitions. The glass transition can further be fine tuned by adding either plasticizers or co-resins.

EXAMPLE 4

Clear coating suitable for automotive applications or wood—The standard additives like anti foaming agents, wetting agents, flow additives and UV stabilizers are added to the MXDA aspartic resin. This mixture will form the A component of a solvent free fast curing clear coat with improved hardness, scratch resistance, and excellent weather ability. The equivalent weight of the resin is 240 and its density is 1.05.

The B Component for making a clear coat is plain aliphatic isocyanate. All standard aliphatic isocyanates can be used. Examples are TMXDI, Desmodur 3300, 3400 and 3600, or isophorone diisocyanate. Mixtures of various aliphatic isocyanates can be used to optimize the properties of the coating.

The clear coating is applied by means of a plural component spray gun with static mixers in line. It is also possible to use a plural component spray gun which is well known in the industry under the name Gussmeyer.

Clear coatings applied this way were dry to touch within 10 minutes and were fully cured after just a few hours. No baking or heating was required and as such this constitutes a very environmentally friendly alternative to all existing clear coats that require the use of solvents and a heat cure and or the use of catalysts which might be harmful to the environment.

EXAMPLE 5

Pigmented top coat suitable for aluminum or steel—The MXDA aspartic resin can be formulated into a pigmented coating by incorporating various pigments like $TiO_2$, fillers like carbonates or silicates, defoamers and flowing agents, as well as UV stabilizers. This mixture is milled in the usual way well known to the coating industry and will form component A. No solvents or catalysts are added.

The B component is the same as in Example 4. The choice of the isocyanate will determine largely the properties of the coating. Adhesion to well-prepared steel or aluminum is outstanding.

The pigmented top coating is preferably applied by means of a twin feed plural component spray gun with a static mixer in line or by means of the so called Gussmeyer Gun.

Obviously, many modifications and variations are possible in light of the above teachings. It is therefore to be understood that the claimed subject matter may be practiced otherwise than as specifically described. Any reference to claim elements in the singular, e.g., using the articles "a," "an," "the," or "said" is not construed as limiting the element to the singular.

What is claimed is:

1. A method comprising:
providing a polyisocyanate and the compound

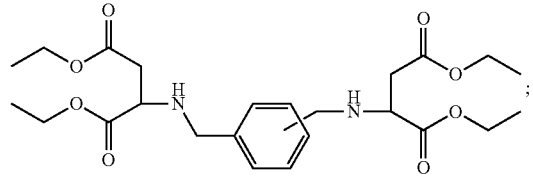

spraying the polyisocyanate and the compound with a plural component pump onto a surface to form a mixture; and
allowing the mixture to cure to a polyurea;
wherein the compound is the only isocyanate-reactive compound used to make the polyurea.

2. The method of claim 1, wherein the polyurea is made in the absence of solvent.

3. The method of claim 1, wherein the polyisocyanate has an isocyanate equivalent weight of 100 to 200.

4. The method of claim 1, wherein the polyisocyanate is an aliphatic polyisocyanate.

5. The method of claim 1, wherein the polyisocyanate is α,α,α',α'-tetramethylxylylene diisocyanate or isophorone diisocyanate.

* * * * *